United States Patent
Saitoh

(10) Patent No.: US 8,568,287 B2
(45) Date of Patent: Oct. 29, 2013

(54) FIXTURE OF THE HEAD FOR TRANSCRANIAL MAGNETIC STIMULATION AND TRANSCRANIAL MAGNETIC STIMULATOR

(75) Inventor: Youichi Saitoh, Osaka (JP)

(73) Assignees: Osaka University, Osaka (JP); Teijin Pharma Limited, Tokyo (JP)

( * ) Notice: Subject to any disclaimer, the term of this patent is extended or adjusted under 35 U.S.C. 154(b) by 1089 days.

(21) Appl. No.: 12/226,473

(22) PCT Filed: Apr. 18, 2007

(86) PCT No.: PCT/JP2007/058411
§ 371 (c)(1),
(2), (4) Date: Feb. 9, 2009

(87) PCT Pub. No.: WO2007/123147
PCT Pub. Date: Nov. 1, 2007

(65) Prior Publication Data
US 2009/0187062 A1 Jul. 23, 2009

(30) Foreign Application Priority Data
Apr. 18, 2006 (JP) ................................. 2006-114116

(51) Int. Cl.
*A61N 2/02* (2006.01)
(52) U.S. Cl.
USPC .......................................................... 600/13
(58) Field of Classification Search
USPC ....................................................... 600/1–15
See application file for complete search history.

(56) References Cited

U.S. PATENT DOCUMENTS

| | | | |
|---|---|---|---|
| 6,926,660 B2* | 8/2005 | Miller | 600/9 |
| 7,290,548 B2* | 11/2007 | Ungemach et al. | 128/869 |
| 2010/0113959 A1* | 5/2010 | Pascual-Leone et al. | 600/544 |

FOREIGN PATENT DOCUMENTS

JP         07-148279 A      6/1995
(Continued)

OTHER PUBLICATIONS

European Extended Search Report for EP application No. 07741847.3, dated Oct. 12, 2010.

(Continued)

*Primary Examiner* — Charles A Marmor, II
*Assistant Examiner* — Catherine E Burk
(74) *Attorney, Agent, or Firm* — Rader, Fishman & Grauer PLLC

(57) ABSTRACT

A transcranial magnetic stimulator according to the present invention includes fixing means for detachably fixing a magnetic field generating means and contains a fixture of a head which covers a head of an examinee to be fixed engaged with a shape of the head that is inherent to an examinee; and characterized in that: a relative position of the magnetic field generating means with respect to the head of the examinee is held constant so that the highest point of an intensity of an electric current to be induced by a magnetic field to be generated by the magnetic field generating means is constantly arranged on a target spot of a diameter not more than 10 mm, which depends on each of the examinees and is located within a cranium, by fixing the magnetic field generating means to the fixing means and a direction of a magnetic field to be generated by the magnetic field generating means and a direction of the target spot are made into a fixed relation.

3 Claims, 12 Drawing Sheets
(1 of 12 Drawing Sheet(s) Filed in Color)

(56) References Cited

FOREIGN PATENT DOCUMENTS

| | | |
|---|---|---|
| JP | 10-076020 A | 3/1998 |
| WO | WO-03/098268 A1 | 11/2003 |
| WO | WO-2004/032781 A1 | 4/2004 |
| WO | WO-2004/080526 A2 | 9/2004 |
| WO | WO-2004/080527 A2 | 9/2004 |

OTHER PUBLICATIONS

Azuma Hirayama et al., "Reduction of intractable deafferentation pain by navigation-guided repetitive transcranial magnetic stimulation of the primary motor cortex", International Association for the Study of Pain, Elservier B.V., Pain 122(2006) pp. 22-27, (2006).

International Search Report mailed on Jul. 24, 2007.

\* cited by examiner

Fig.2
(1)
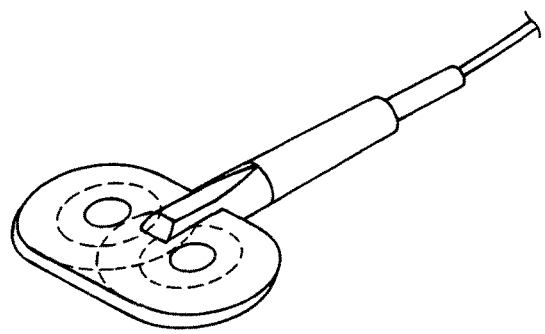
(2)
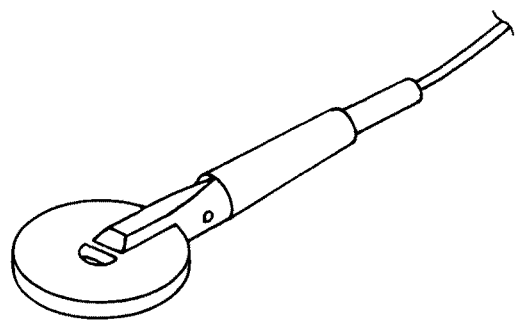
(3)
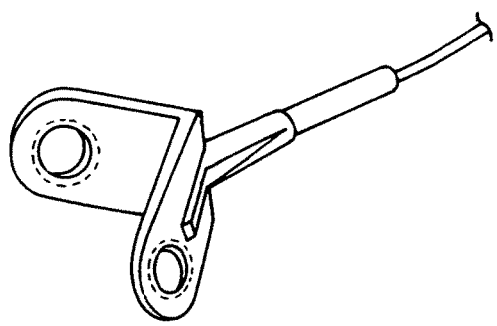

FIXTURE OF THE HEAD FOR TRANSCRANIAL MAGNETIC STIMULATION AND TRANSCRANIAL MAGNETIC STIMULATOR

TECHNICAL FIELD

The present invention relates to a repetitive transcranial magnetic stimulator, which reduce deafferentation pain (a neuropathic pain) due to a repetitive transcranial magnetic stimulation.

BACKGROUND ART

In recent years, it has been informed that a pain reduction effect against deafferentation pain, which is identical with an electric stimulation, can be obtained by a repetitive transcranial magnetic stimulation (rTMS) to stimulate a brain cortex neuron (refer to, e.g., Non-Patent Document 1). The repetitive transcranial magnetic stimulation is a method to generate a weak magnetic field and electric currents in a brain cortex neuron using a principle of an electromagnetic induction by instantaneously passing a current through a coil (see FIG. 6) and stimulate the brain cortex neuron noninvasively.

FIG. 9 shows a conventional transcranial magnetic stimulator for carrying out a repetitive transcranial magnetic stimulation. The conventional transcranial magnetic stimulator is schematically configured by a magnetic stimulation control device 10', magnetic field generating means 8' including a coil, and a cable 7' to connect them. The magnetic stimulation control device 10' generates an electric current pulse of a relatively high frequency (for example, 5 Hz to 20 Hz) continuously or intermittently. The magnetic field generating means 8' includes a coil, through which electric current pulse from the magnetic stimulation control device 10' passes, therewithin. A magnetic field to be generated by this coil is applied from the outside of a cranium of an examinee to the brain cortex neuron so as to stimulate the brain cortex neuron.
Non-Patent Document 1: "Reduction of intractable deafferentation pain with navigation-guided repetitive transcranial magnetic stimulation (rTMS) of the primary motor cortex", A. Hirayama, Y. Saitoh et al., PAIN 122: 22-27, 2006

DISCLOSURE OF INVENTION

Problems to be Solved by the Invention

On the other hand, the inventors have been earnestly studying on reduction of deafferentation pain by using the above-described transcranial magnetic stimulator and they have obtained the following perceptions.

(1) In order to improve a pain reduction effect, a target in the brain cortex as an object of magnetic stimulation, is formed like a spot, which is inherent for each examinee having a predetermined case. In other words, a position of the target, an angle of the magnetic field, and a direction of the coil are basically unambiguous for the examinee who has a certain case. Specifically, the target becomes an area with a diameter about 10 mm, and in order to stimulate such a spot-like target, it is better that direction characteristics of the magnetic field generating means are extremely high.

(2) In consideration of the above-described (1), carrying out the repetitive transcranial magnetic stimulation, the pain reduction has been continued for several hours. However, the pain reduction effect has not been continued for several days. As a result, it is preferable to continuously carry out the above-described method every day if possible without much time intervals in view of reduction of a pain.

On the other hand, a following problem is caused. Specifically, the conventional apparatus has a large scale, and extremely wide space and extremely large facilities are needed in order to carry out a magnetic stimulation treatment using the conventional apparatus. Further, it is very difficult to add magnetism to the spot-like target (the position, the direction, and the angle) of the brain cortex.

Based on the above perception, according to the repetitive transcranial magnetic stimulation, (A) the entire apparatus is minimized and simplified; (B) further, it is found that a transcranial magnetic stimulator such that an examinee (a patient) who is a public can ordinarily add a similar magnetic stimulus to the target spot of the brain cortex has been required, and then, the present invention has been completed.

In other word, an object of the present invention provides a repetitive transcranial magnetic stimulator, which can effectively carry out a transcranial magnetic stimulation, and this transcranial magnetic stimulator is simplified and minimized so that an examinee can carry out the transcranial magnetic stimulation at a clinic or at home continuously and repeatedly on a daily basis.

Means for Solving the Problem

The present invention has been made to attain the above-described object. A fixture of a head (for example, a helmet or the like) for a transcranial magnetic stimulation according to the present invention is characterized in that:
comprising fixing means for detachably fixing magnetic field generating means, the fixture of the head covering a head of an examinee to be fixed engaged with a shape of the head that is inherent to an examinee, wherein,
the magnetic field generating means being fixed with the fixing means,
a relative positional relation of the magnetic field generating means with respect to the head of the examinee is held constant so that the highest point of an intensity of an electric current to be induced by a magnetic field to be generated by the magnetic field generating means is constantly arranged on a target spot of a diameter not more than 10 mm, which depends on each of the examinees and is located within a cranium, and a direction of a magnetic field to be generated by the magnetic field generating means and a direction of the target spot are made into a fixed relation.

In addition, a transcranial magnetic stimulator according to the present invention is characterized by: including a fixture of a head for a transcranial magnetic stimulation according to the present invention;
a magnetic field generating means including a coil to be detachably fixed to the fixture of the head; and
a magnetic stimulation control device, which induces a magnetic field by passing an electric current through the coil of the magnetic field generating means.

Effect of the Invention

By using the fixture of the head for a transcranial magnetic stimulation and the transcranial magnetic stimulator according to the present invention, it is possible to carry out the transcranial magnetic stimulation repeatedly and continuously on a daily basis.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2 is a perspective view of an example of magnetic field generating means (a coil), which is used by a transcranial magnetic stimulator.

FIG. 10(2) is a simulation view of a distribution of a magnetic field to be generated on the surface of the cranium. FIG. 10(3) is a simulation view of a distribution of a magnetic field to be generated on the surface of the brain cortex. FIG. 10(4) is a simulation view of a distribution of an electric current (a density of an electric current) on the surface of the brain cortex to be induced by a magnetic field to be generated.

DESCRIPTION OF REFERENCE NUMERALS

2 . . . fixture of head for magnetic stimulation, 4 . . . main body of fixture of head, 6 . . . mesh-like shell part, 8 . . . magnetic field generating means, 10 . . . magnetic stimulation control device, 12 . . . fixture, 14 . . . coil fixing means, 19 . . . fixing table, 20 . . . mesh-like shell, 21 . . . computer, 24 . . . first position displaying means, 26 . . . second position displaying means, 28 . . . optical position grasping means.

BEST MODE FOR CARRYING OUT THE INVENTION

Hereinafter, with reference to the drawings, preferred embodiments of the present invention will be described. In the present specification, a direction of the magnetic field generating means (the coil) is a direction of magnetic field generating mean (a coil) on a surface of a head of an examinee, and an angle of the magnetic field generating mean (the coil) is an angle made by a normal line of the surface of the head of the examinee and a direction of a magnetic field.

First Embodiment

Figure 1:
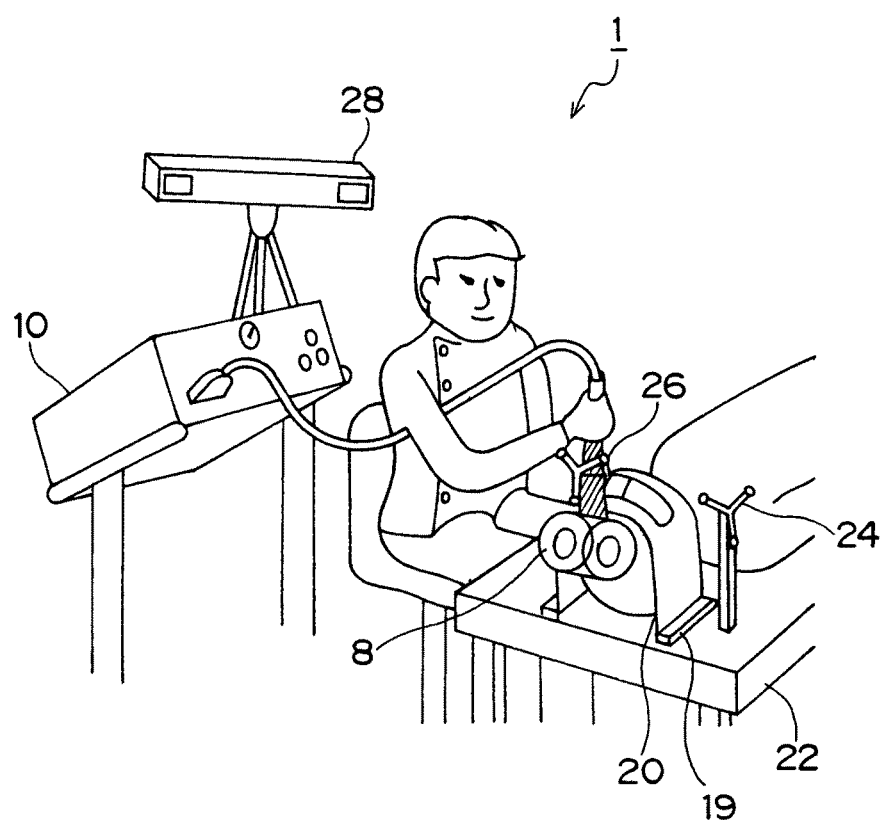
FIG. 1 is an entire view of a transcranial magnetic stimulator according to a first embodiment of the present invention.

FIG. 1 is a schematic view of a repetitive transcranial magnetic stimulator according to a first embodiment of the present invention, of which entire is represented by 1. A transcranial magnetic stimulator 1 according to the first embodiment includes a transcranial magnetic stimulation control device 10, magnetic field generating means 8 including a coil, and a cable to connect them. Further, the transcranial magnetic stimulator 1 according to the first embodiment includes an optical navigation guide system. The optical navigation guide system includes a computer 21 shown in FIG. 3, optical position grasping means 28 that is connected to the computer 21, first position displaying means 24 that is fixed on a treatment bed 22, and second position displaying means 26 that is attached to the magnetic field generating means 8.

An operator who uses the transcranial magnetic stimulator 1 according to the first embodiment can stimulate a brain cortex while confirming a target based on an MRI (magnetic resonance imaging) image of the brain cortex of an examinee to be displayed on the display of the computer 21 and monitoring the position of the coil and the direction and the angle with respect to the surface of the brain in real time. The display of the MRI image of the brain cortex of the examinee and the display of the relative position of the coil (the magnetic field generating means) with respect to the brain cortex are carried out by the optical navigation guide system. The optical navigation guide system shown in FIG. 1 is based on a Brainsight Frameless Navigation system (registered trade mark) (Rogue Research Inc, Motreal, Canada).

Prior to the treatment due to the transcranial magnetic stimulator 1, at first, the MRI image of the head of the examinee having a marker attached is taken, and based on this, a three-dimensional image of a brain surface is built up by the computer 21. Next, positioning of the head of the examinee is made on the treatment bed 22. In this time, the head is covered with the mesh-like shell 20 for each examinee, and the position and the shape of the head in this time are saved by the mesh-like shell 20 and its fixing table 19 for each examinee. It is desirable that this mesh-like shell 20 is a mesh-like shell made of a thermoplastic resin to be used for a stereotactic radio surgery. The mesh-like shell 20 can save the shape of the head by its thermal plasticity. As a result, by fixing the head of the examinee using the mesh-like shell 20, of which shape is saved, and the fixing table 19 after this MRI imaging operation and saving operation, a fixed position of the head of each examinee can be accurately reproduced on the treatment bed 22.

Upon this positioning of the head, the position of a marker attached to the head of the examinee and the position of the first position displaying means 24 to be fixed on the treatment bed 22 are grasped by the computer 21 via the optical position grasping means 28 (to be described later). Further, the position data of a marker that is attached to the head of the examinee and the marker data on the MRI three-dimensional image are connected by the computer 21. Thus, the computer 21 is capable of grasping the MRI image, the position of the head (the brain) of the examinee, and the position of the treatment bed 22 by connecting them.

Next, upon practicing the transcranial magnetic stimulation due to the repetitive transcranial magnetic stimulator 1 shown in FIG. 1, laying the examinee on the treatment bed 22 and fixing the face of the head of the examinee by the mesh-like shell 20, the head of the examinee during a stimulus treatment is prevented from being moved.

In the optical navigation guide system, the relative position of the magnetic field generating means 8 to be used with respect to the head of the examinee can be grasped by the computer 21. In other words, the optical position grasping means 28 continuously grasps the position of the first position displaying means 24 to be fixed on the treatment bed 22 and the position of the second position displaying means 26 to be attached to the magnetic field generating means 8. The optical position grasping means 28 provides the first position information of the first position displaying means 24 and the second position information of the second position displaying means 26 to the computer 21, to which the optical position grasping means 28 is connected. If the computer 21 grasps the relative position information of the above-described brain (the head) of the examinee with respect to the treatment bed 22, the position, the direction, and the angle of the magnetic field generating means 8 with respect to the brain cortex of the examinee can be calculated in real time to be displayed according to this relative position information, the above-described first position information, and the above-described second position information.

Figure 3:
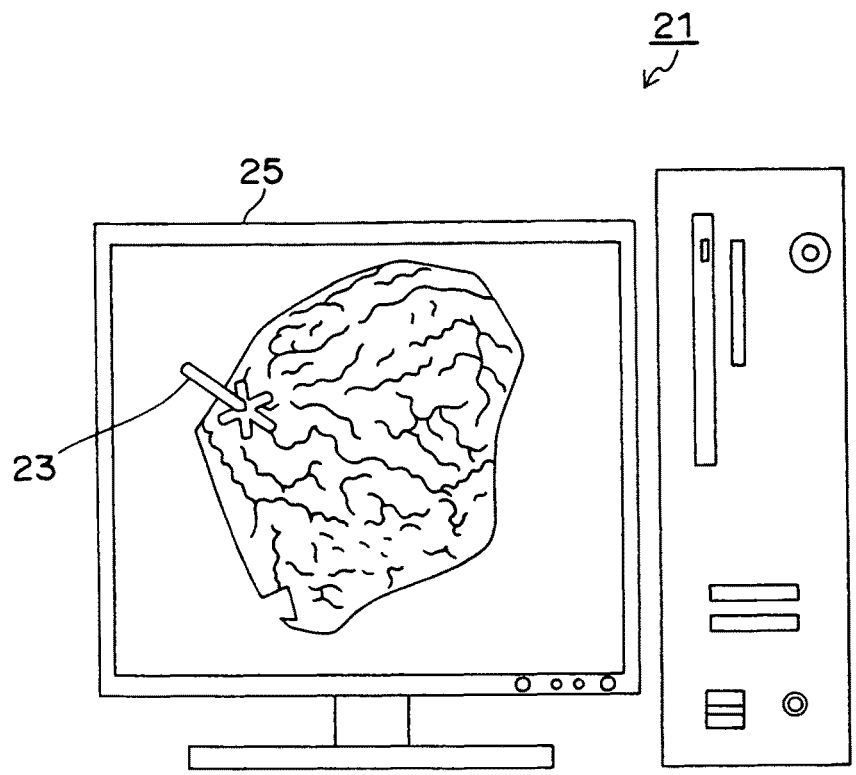
FIG. 3 shows a computer of an optical navigation guide system to display an MRI image of a brain cortex and an arrow of a magnetic field.

As shown in FIG. 3, the computer 21 displays the MRI image of the brain cortex, and the position, the direction, and the angle of the magnetic field generating means 8. In FIG. 3, an arrow 23 represents the positions, the directions, and the angles of the magnetic field generating means 8 and the generated magnetic field.

The head is fixed to a fixed position of the treatment bed 22, which is inherent to the examinee, and then, an electric current pulse generated by the cranial magnetic stimulation control device 10 is continuously passed through the coil within the magnetic field generating means 8. The operator stimulates the appropriate position of the brain cortex while confirming the MRI image of the examinee on the display 25 of the computer 21 and the information of the magnetic field generating means.

FIG. 2 is a perspective view of the magnetic field generating means (coil) 8 to be used for a repetitive transcranial magnetic stimulator. The magnetic field generating means shown in FIG. 2(2) includes a circular coil. The magnetic field generating means in this case is easily fixed and is suitable for exercising stimulation in a wide range. On the other hand, the magnetic field generating means shown in FIG. 2(1) is configured by aligning two circular coils in a figure of eight on the same plane, and an electric current passes through two coils in a reverse direction. The magnetic field generating means shaped in a figure of eight has the highest density of an inductance electric current just below a point that is equivalent to a cross point of a figure of eight, and this magnetic field generating means is suitable for exercising localized stimulation although it is difficult to fix. Further, the magnetic field generating means shown in FIG. 2(3) is configured by arranging two coils across a predetermined angle to be formed in a mountain shape (for example, a shape referred to as a double corn shape). It is preferable that any magnetic field generating means 8 shown in FIGS. 2(1), 2(2), and 2(3) is molded by a resin.

Figure 4:
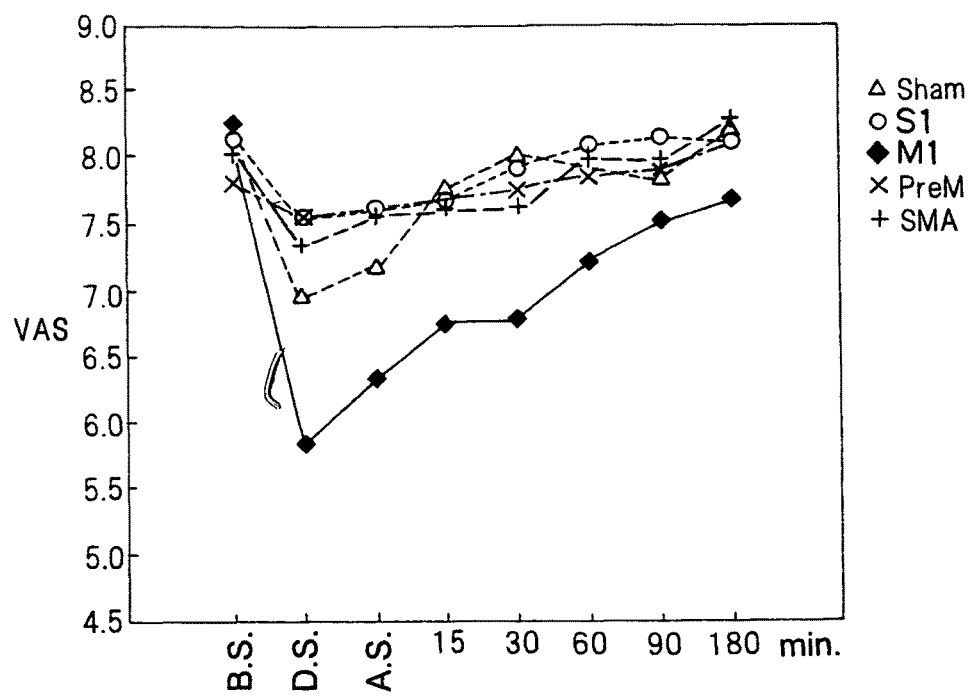
FIG. 4 is a graph for showing a transition of the average values of a VAS before stimulation (B.S.), during stimulation (D.S.), just after stimulation (A.S.), and after 30 minutes, 60 minutes, 90 minutes, and 180 minutes of stimulation when the repetitive transcranial magnetic stimulation due to the transcranial magnetic stimulator according to the first embodiment of the present invention is applied to twenty examinees.

FIG. 4 is a graph for showing a transition of the average values of a VAS (Visual Analogue Scale) before stimulation, during stimulation, just after stimulation, and after 30 minutes, 60 minutes, 90 minutes, and 180 minutes of stimulation when the repetitive transcranial magnetic stimulation due to the repetitive transcranial magnetic stimulator according to the first embodiment of the present invention is applied to twenty examinees. The VAS in this case is a scale of pain of the examinee and is selected by the examinee himself or herself from among the values of "0" to "10". "0" shows a state that the examinee does not feel any pain, and "10" shows a state that the examinee feels the most acute pain.

The stimulation conditions are as follows:
(1) The magnetic field generating means includes a coil shaped in a figure of eight.
(2) The intensity is 90% of a resting motor threshold.
(3) The frequency of stimulation is 5 Hz.
(4) The stimulation of 50 times is carried out in ten times with a stimulation time 10 seconds and a stimulation interval 50 seconds. Therefore, this results in that the stimulation is made 500 times in total.

With respect to the resting motor threshold, at first, stimulating the primary motor area, a motor threshold is decided (with respect to the examinee, whose resting motor threshold cannot be measured, his or her resting motor threshold is uniformly defined as 100 A/µs). The stimulation targets are defined as four places, namely, a primary motor area (M1), a primary sensory area (S1), a supplementary motor area (SMA), and a prefrontal area (preM). Sham stimulation is also made.

As being obvious from the graph, if the stimulation is given to the primary motor area (M1), the VAS that is about 8.2 just before the stimulation is decreased to about 5.8 during the stimulation, and the VAS value has been maintained about 7.5 even after 180 minutes although the VAS value is gradually increased. In other regions, the VAS tends to be decreased during the stimulation and after the stimulation, however, descent is not remarkable. As a result, it seems that an effective pain reduction effect can be obtained only in the stimulation to the primary motor area (M1), and it can be said that the effect of reduction of pain has been continued for several hours (in the graph of FIG. 4, at least 180 minutes) after the stimulation.

As described above, the inventors have obtained the following new perceptions because of earnest studying on reduction of deafferentation pain by using the transcranial magnetic stimulator. A target in the brain cortex as an object of a magnetic stimulation for improving a pain reduction effect is formed like a spot, which is inherent for each examinee having a predetermined case. In other words, a position of the target, an angle of the magnetic field, and a direction of the coil are basically unambiguous for the examinee who has a certain case. Therefore, if the repetitive transcranial magnetic stimulator 1 according to the first embodiment of the present invention is used particularly together with the magnetic field generating means including the coil in a figure of eight, it is possible to effectively stimulate the spot-like target, which is inherent for each examinee having various cases by the optical navigation guide system. The size of this spot-like target does not exceed a diameter 20 mm according to a perception due to study of the inventors. It is also turned out that the area of this spot-like target is preferably not more than a diameter 10 mm.

As explained above, for example, the magnetic field generating means shaped in a figure of eight has the highest density of an inductance electric current just below a point that is equivalent to a cross point of a figure of eight, namely, along a normal line passing through the cross point of a figure of eight. Accordingly, it is preferable that a relation between the magnetic field generating means and the cranium is decided and held so as for a line having the highest density of the inductance electric current to penetrate through substantially a center portion of the above-described target spot with a diameter not more than 10 mm in the brain cortex, which is inherent for each examinee having various cases, as possible. It is preferable that the relation between the magnetic field generating means and the cranium is decided and held so that the line having the highest density of the inductance electric current penetrates the target spot in a constant direction. The same applies to the magnetic field generating means of other shapes.

Figure 10:
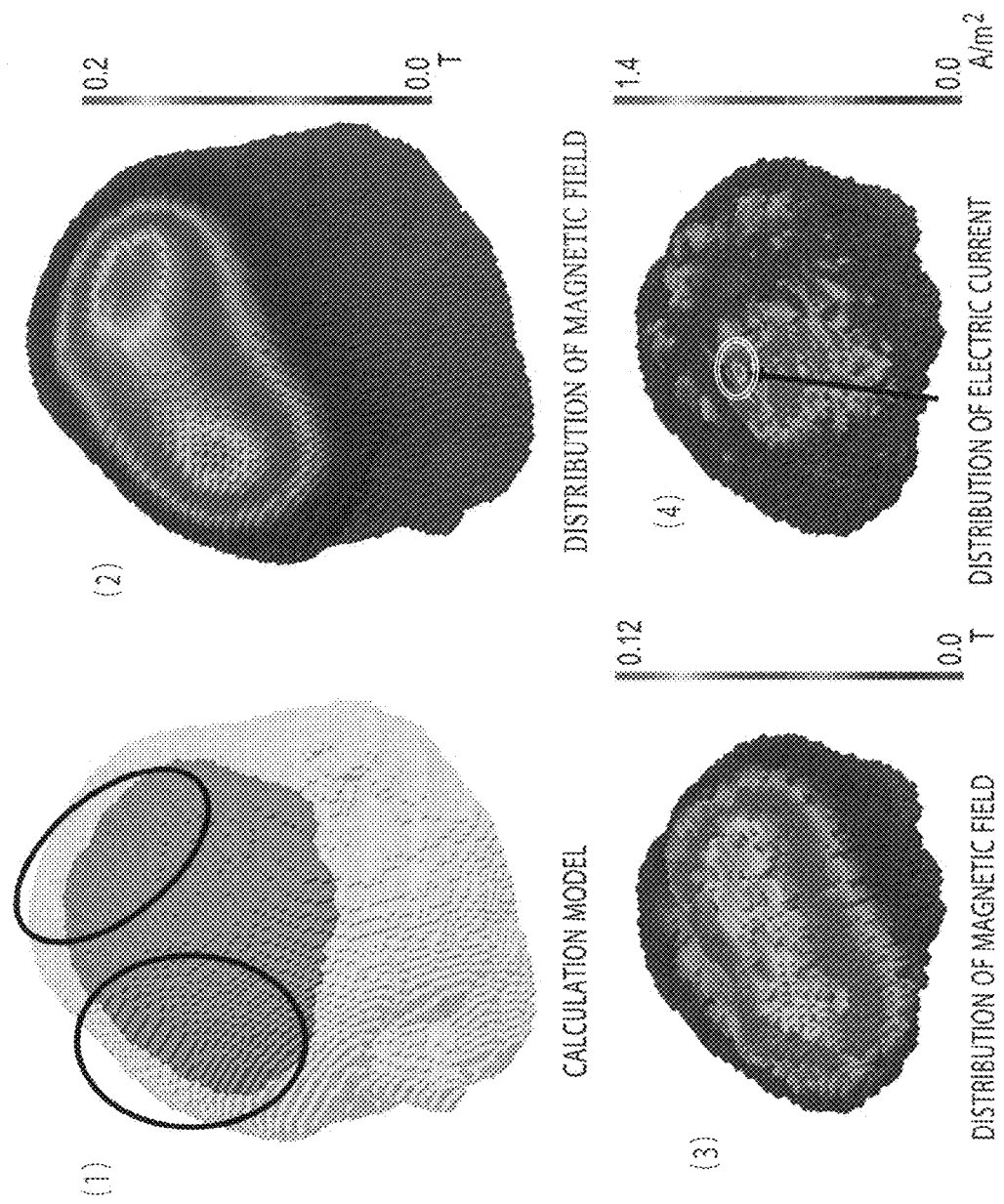
FIG. 10 is a simulation view showing a surface of a cranium, a distribution of a magnetic field to be generated on the surface of the brain cortex, and a distribution of an electric current when aligning two circle coils on the surface of the cranium and virtually passing an electric current through each of the two circle coils. Two circle coils shown in FIG. 10(1) are equivalent to the magnetic field generating means shaped in a figure of eight shown in FIG. 2(1).

FIG. 10 is a simulation view showing a surface of a cranium, a distribution of a magnetic field to be generated on the surface of the brain cortex, and a distribution of an electric current when aligning two circle coils on the surface of the cranium and virtually passing an electric current through each of the two circle coils. Two circle coils shown in FIG. 10(1) (shown by two ellipses in the Figure) are equivalent to the magnetic field generating means shaped in a figure of eight shown in FIG. 2(1). FIG. 10(2) is a simulation view of a distribution of a magnetic field to be generated on the surface of the cranium. FIG. 10(3) is a simulation view of a distribution of a magnetic field to be generated on the surface of the brain cortex. Further, FIG. 10(4) is a simulation view of a distribution of an electric current (a density of an electric current) on the surface of the brain cortex to be induced by a magnetic field to be generated. A unit of the distribution of the magnetic field is a tesla (T) and a unit of an electric current distribution is $A/m^2$. As shown by an arrow and an elliptic circle on a left-upper part of a center of FIG. 10(4), a region having a high density of an electric current on the brain cortex appears as a point. It is preferable that this point is included in a target spot (penetrates through a target spot) with a diameter not more than 10 mm, which is inherent for each examinee.

In the meantime, to begin with, it has been found out that the repetitive transcranial magnetic stimulation is effective not only in easing of pain but also in treatment for a depression and promotion of rehabilitation after a stroke. In addition, in easing of pain, it has been determined that the object of stimulation is mainly a primary motor area (M1); however, in a treatment for a depression, the prefrontal area is defined as the object of stimulation, and in a rehabilitation promotion method after a stroke, a healthy side in the same primary motor area (an affected side in easing of pain) is defined as the object of stimulation. Further, even in pain of the same case in curing of easing of pain, the region of the primary motor area, which is the object of stimulation, depends on the examinee (the patient) in many cases.

In addition, the repetitive transcranial magnetic stimulator 1 according to the above-described first embodiment has a large scale, and extremely wide space and extremely large facilities are needed. As a result, it is not easy to install this apparatus for each home of the examinee. Further, the professional operator should always help the examinee.

Therefore, it can be said that to provide the repetitive transcranial magnetic stimulator is preferable, which can effectively stimulate the spot-like target inherent for each examinee having various cases and can be simply used.

Second Embodiment

Figure 5:
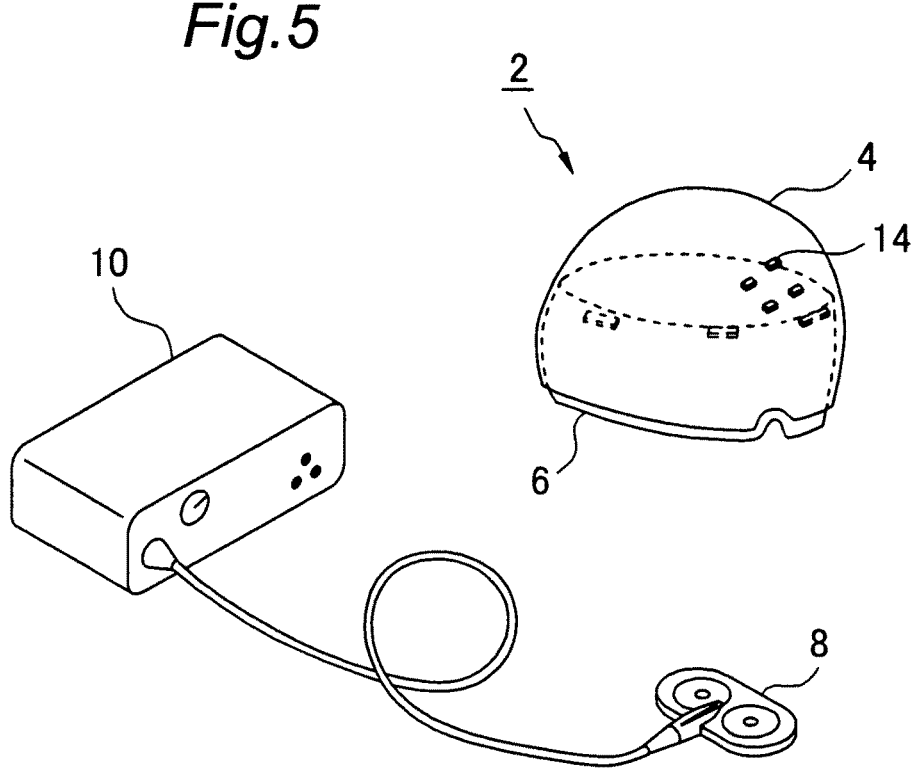
FIG. 5 is an entire view of a repetitive transcranial magnetic stimulator according to a second embodiment of the present invention.

FIG. 5 is an entire view of a repetitive transcranial magnetic stimulator according to a second embodiment of the present invention. It is assumed that the repetitive transcranial magnetic stimulator according to the second embodiment of the present invention is provided with the following conditions.

(1) Facilities are not large and they are minimized and simplified so that the examinee can carry out the transcranial magnetic stimulation at his or her home or the like on a daily basis.

(2) As the inventors found, the region of the stimulation target is narrow and fixed in accordance with the case of the examinee. As a result, it is ensured that the magnetic stimulation due to the coil can be always given to the same region of the brain of the patient from the same direction and angle.

In the repetitive transcranial magnetic stimulator shown in FIG. 5, the magnetic field generating means (coil) 8 is connected to the magnetic stimulation control device 10, and an electric current pulse generated by the magnetic stimulation control device 10 continuously passes through the magnetic field generating means (coil) 8 so as to discharge an electric current. These magnetic stimulation control device 10 and magnetic field generating means 8 may be identical with those of the first embodiment shown in FIG. 1, however, it is preferable to more minimize and simplify the magnetic stimulation control device 10 and the magnetic field generating means 8 by configuring the magnetic stimulation control device 10 by an appropriate semiconductor circuit element or the like.

Further, the repetitive transcranial magnetic stimulator according to the second embodiment of the present invention includes a fixture for fixing the magnetic field generating means 8 to the head, namely, a fixture of head for magnetic stimulation 2. For example, the fixture of the head here may be a helmet or the like. A right part of FIG. 5 shows a perspective view of the fixture of head for magnetic stimulation 2 according to the second embodiment of the present invention.

The above-described fixture of head for magnetic stimulation 2 is mainly configured by a mesh-like shell part 6 and a main body of a fixture of the head 4. The mesh-like shell part 6 and the main body of the fixture of the head 4 are formed so that they are attached firmly to each other without a gap in accordance with the shape of the head (including a nasal point) of the examinee as much as possible for each examinee. In the mesh-like shell part 6 and the main body of the fixture of the head 4, a relative arrangement position is fixed by an appropriate fixture as described later. Further, in FIGS. 5 to 8, it is assumed that the mesh-like shell part 6 and the main body of the fixture of the head 4 are individual members. As described later, the mesh-like shell part 6 and the main body of the fixture of the head 4 may be formed in an integrated fashion.

Figure 6:
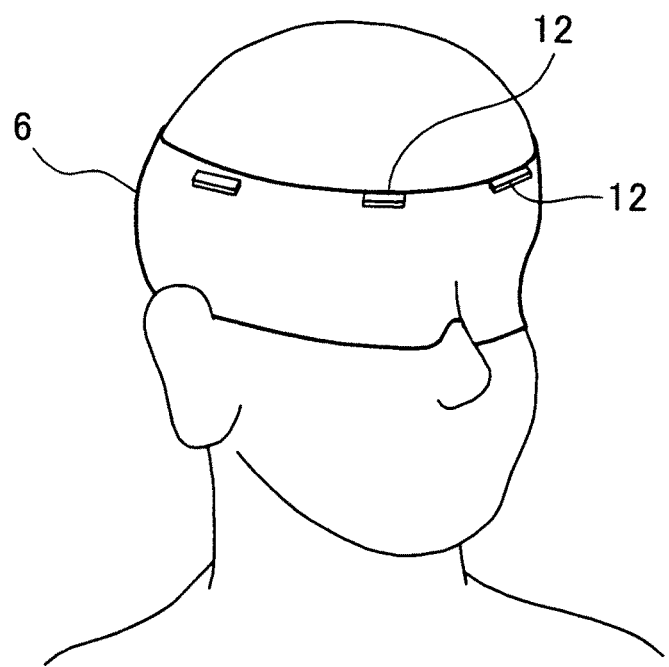
FIG. 6 is a perspective view showing a state in which a mesh-like shell part is mounted on a head.
Figure 7:
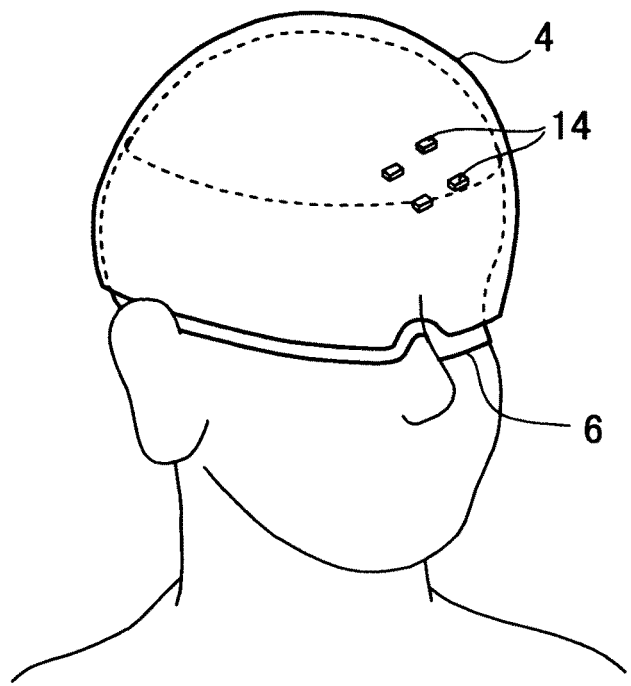
FIG. 7 is a perspective view showing a state in which the mesh-like shell part wound around the head is covered with a main body of a fixture of a head with respective corresponding fixture and fastening member being engaged with each other.
Figure 8:
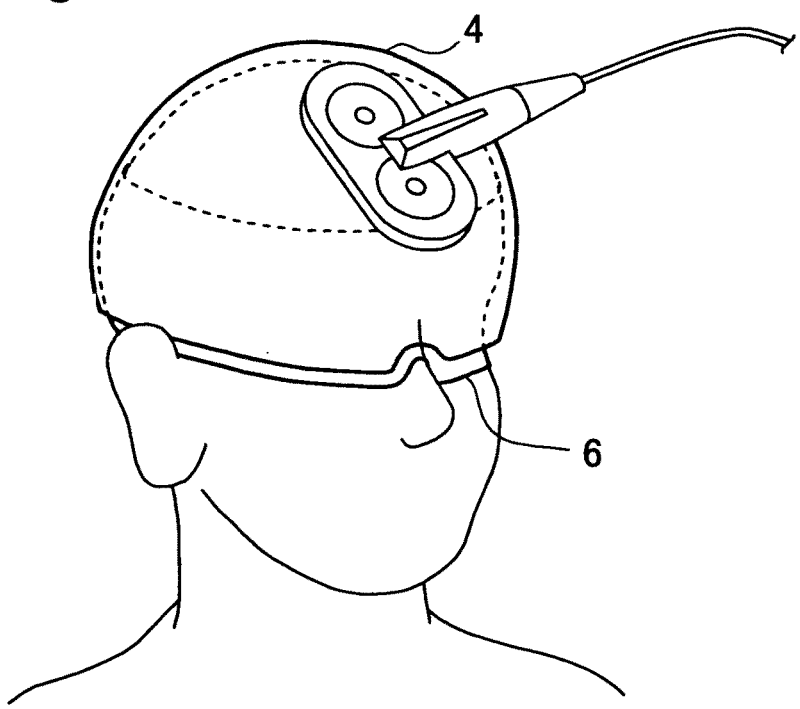
FIG. 8 is a perspective view showing a state in which coil fixing means that is mounted on the main body of the fixture of the head is engaged with a coil fixing means receiving member of the magnetic field generating means to fix the magnetic field generating means to the main body of the fixture of the head.
Figure 9:
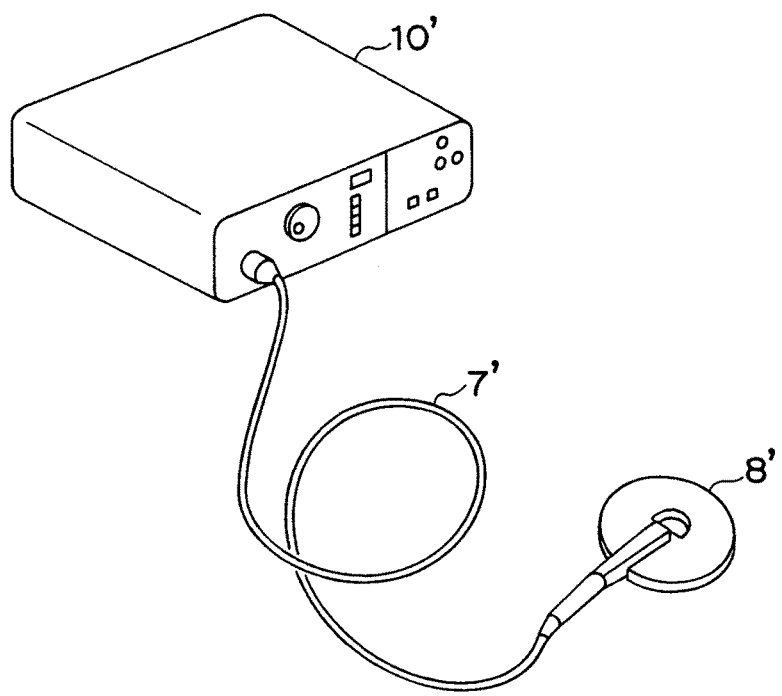
FIG. 9 is a perspective view of a conventional transcranial magnetic stimulator.

FIGS. 6 to 8 are perspective views showing the manners that the fixture of head for magnetic stimulation 2 and the magnetic field generating means 8 are mounted on the head in sequence. At first, as shown in FIG. 6, the mesh-like shell part 6 to wind the head including the nasal port substantially in a belt-like shape is mounted. In FIG. 6, individual minute mesh-shapes are omitted. The material of the mesh-like shell part 6 is not limited to a particular one. For example, it is preferable that the mesh-like shell part 6 is a mesh made of a thermoplastic resin to be used for a stereotactic radio surgery or the like as with the first embodiment. In other words, it is preferable that the mesh-like shell part 6 is formed by a thin mesh-like material, which is formed into a plastic when it is provided with heat to be easily mounted on the head while saving (storing) the shape of the head of the individual examinee having the nasal port in the center. Further, the shell part may be not formed in a mesh-like shape as far as it has such a keeping quality of a shape and a thermal plasticity. As described above, since the mesh-like shell part 6 saves (stores) the shape of the head having the nasal point in the center, the relative arrangement position between the mesh-like shell part 6 and the head is always fixed even if attachment and detachment are repeated.

Further, it is ensured that the mesh-like shell part 6 shown in FIG. 6 is always mounted on the same position of the head mainly depending on the shape of the nasal port. Here, the mesh-like shell part 6 may be always mounted on the same position of the head depending on these shapes and positions saving the shape and the position of ears.

On the surface of the outside of the mesh-like shell part 6, a plurality of fixtures 12 is mounted. A fastening member (not illustrated) corresponding to this fixture 12 is provided on the corresponding position in the inside of the main body of the fixture of the head 4. FIG. 7 is a perspective view showing a state in which the mesh-like shell part 6 wound around the head is covered with the main body of the fixture of the head 4 with respective corresponding fixture 12 and the fastening member (not illustrated) being engaged with each other. Covering the mesh-like shell part 6 with the main body of the fixture of the head 4 and engaging the corresponding fixture 12 and the fastening member (not illustrated) with each other, the relative position of the main body of the fixture of the head 4 corresponding to the mesh-like shell part 6 becomes constant. Accordingly, in this time, the relative position of the main body of the fixture of the head 4 with respect to the head is decided, and this relative position becomes always constant. It is preferable that the main body of the fixture of the head 4 is configured by a thin plate made of a thermoplastic resin.

As shown in FIG. 7, on the surface of the outside of the main body of the fixture of the head 4, coil fixing means 14 is provided. In response to this, on the side of the face of the magnetic field generating means 8 corresponding to the surface of the outside of the main body of the fixture of the head 4, a coil fixing means receiving member (not illustrated) is provided. For example, the coil fixing means 14 is made of a polygonal projection that is projected at a certain angle, and the coil fixing means receiving member is formed by a recessed portion to be engaged with such a projection. When plural sets of the coil fixing means 14 and the coil fixing means receiving members are provided, each coil fixing means 14 may be made of a columnar projection, which is projected at a predetermined angle, and each coil fixing means receiving member may be made of a recessed portion to be engaged with such a projection.

In the first place, the coil fixing means 14 is a separated member from the main body of the fixture of the head 4, and depending on the position where the coil fixing means 14 is mounted, a position where the magnetic field generating means 8 is fixed on the main body of the fixture of the head 4 is decided. In addition, the thicknesses of the coil fixing means 14 and the coil fixing means receiving member (not illustrated) can be changed, and by arbitrarily adjusting the thicknesses of these plural coil fixing means 14 and coil fixing means receiving members (not illustrated), an angle of a magnetic field to be generated by the magnetic field generating means 8 can be adjusted. According to the coil fixing means 14 and coil fixing means receiving member (not illustrated), the relative position of the magnetic field generating means 8 (including the direction and the angle) with respect to the main body of the fixture of the head 4 is decided, so that this relative position becomes constant.

FIG. 8 is a perspective view showing a state in which the coil fixing means 14 that is mounted on the main body of the fixture of the head 4 is engaged with the coil fixing means receiving member (not illustrated) of the magnetic field generating means 8 to fix the magnetic field generating means 8 to the main body of the fixture of the head 4. From above, the arrangement of the magnetic field generating means 8 corresponding to the head (the position, the direction, and the angle) become always constant by means of the mesh-like shell part 6 and the main body of the fixture of the head 4 even in the case that the examinee arranges them transcranial magnetic stimulation by himself or herself.

In the meantime, in the above description relating to the second embodiment, the explanation is progressed on the premise of (A) the mesh-like shell part 6 and the main body of the fixture of the head 4 have been already manufactured so as to be firmly attached to the head of the examinee; (B) the fixture 12 and the fastening member are arranged on the surface of the outside of the mesh-like shell part 6 and on the inside of the main body of the fixture of the head 4 in an appropriate manner; and (c) the coil fixing means 14 and the coil fixing means receiving member (not illustrated) are arranged on the surface of the outside of the main body of the fixture of the head 4 and a coil 8 in a figure of eight in an appropriate manner. These manufacturing operation and arrangement operation as a preparation can be made by using various apparatuses and methods. For example, by using the above-described navigation guide system, these manufacturing operation and arrangement operation may be carried out (refer to a third embodiment).

Then, as described with respect to the first embodiment, it is preferable that a relation between the magnetic field generating means and the cranium is decided and held so that a line having the highest density of the inductance electric current due to the magnetic field generating means penetrates a target spot with a diameter not more than 10 nm in the brain cortex, which is inherent for each examinee having various cases. Further, it is preferable that a relation between the magnetic field generating means and the cranium is decided and held so that the above-described line having the highest density of the inductance electric current penetrates the above-described target spot in a constant direction.

According to the second embodiment, it is an important point that the position, the direction, and the angle of the magnetic field generating means (the coil) for the head, namely, the brain are always held. As a result, if this point is observed, other embodiments to realize the present invention can be also configured. For example, the above-described mesh-like shell part 6 and the main body of the fixture of the head 4 may be formed in an integrated fashion.

In addition, in FIGS. 6 to 9, it is assumed that the magnetic field generating means includes a coil in a figure of eight. The magnetic field generating means may include the circular coil.

Figure 11:
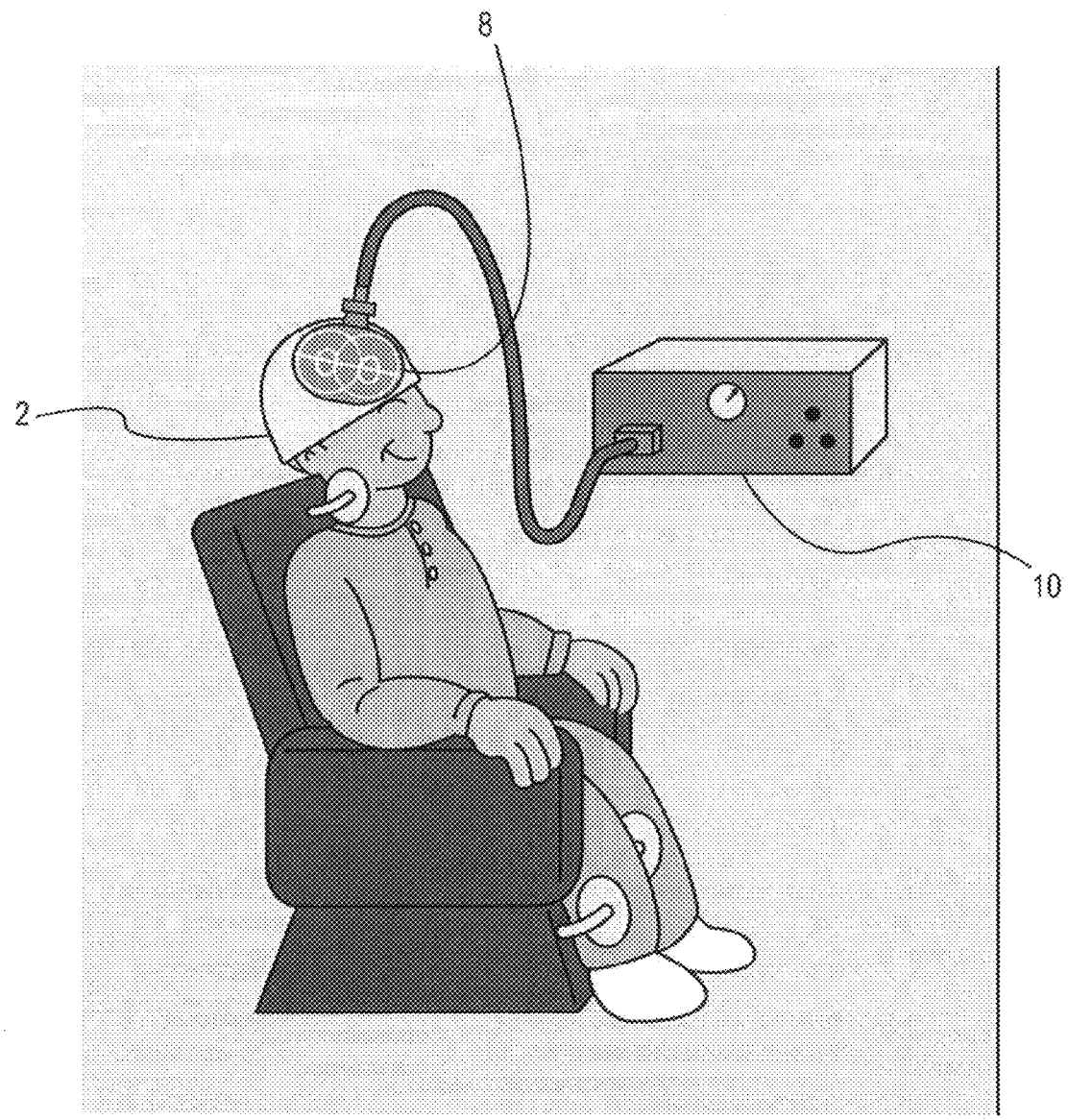
FIG. 11 is a view showing a state in which a patient (an examinee) uses the repetitive transcranial magnetic stimulator according to the second embodiment of the present invention at home or the like on a daily basis without help of a professional operator.

FIG. 11 is a view showing a state therein which a patient (an examinee) uses the repetitive transcranial magnetic stimulator according to the second embodiment of the present invention at home or the like on a daily basis without help of a professional operator. FIG. 11 shows the state in which the examinee wears the fixture of head for magnetic stimulation 2, to which the magnetic field generating means 8 to be connected to the magnetic stimulation control device 10 is fixed.

Third Embodiment

Figure 12:
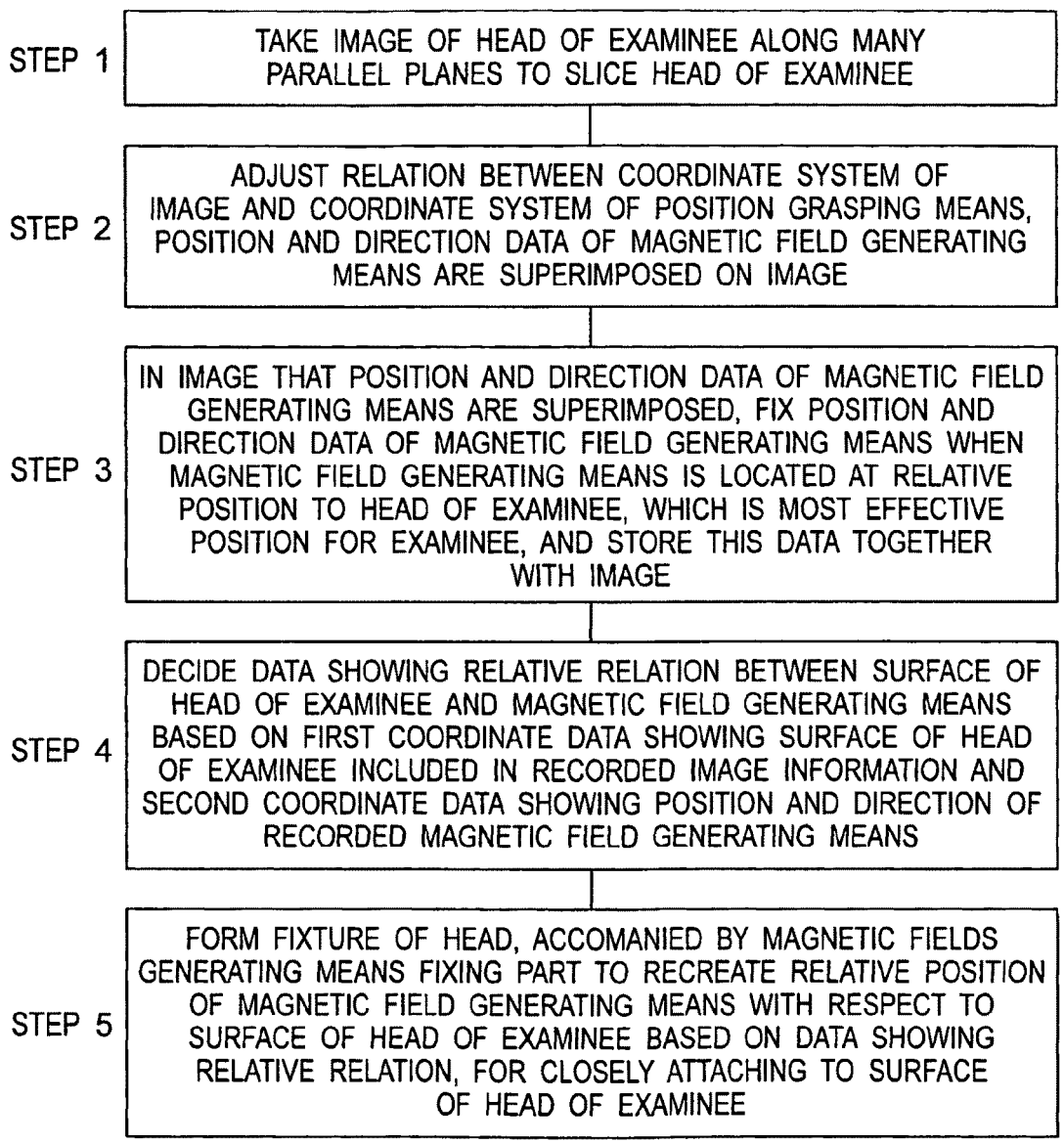
FIG. 12 is a flow chart showing a schematic procedure of a method for manufacturing a fixture of the head according to a third embodiment of the present invention.

A third embodiment according to the present invention to be described below relates to a method for manufacturing a fixture of a head, which decides the appropriate position of the magnetic field generating means for the brain and the cranium of the patient more accurately and automatically by using the repetitive transcranial magnetic stimulator shown in FIG. 1 and the optical navigation guide system shown in FIG. 3 to reflect the position to manufacturing of the fixture of the head, and thereby, faithfully recreates the appropriate position of the magnetic field generating means. FIG. 12 is a flow chart showing a schematic procedure of a method for manufacturing a fixture of the head according to the third embodiment of the present invention.

Figure 13:
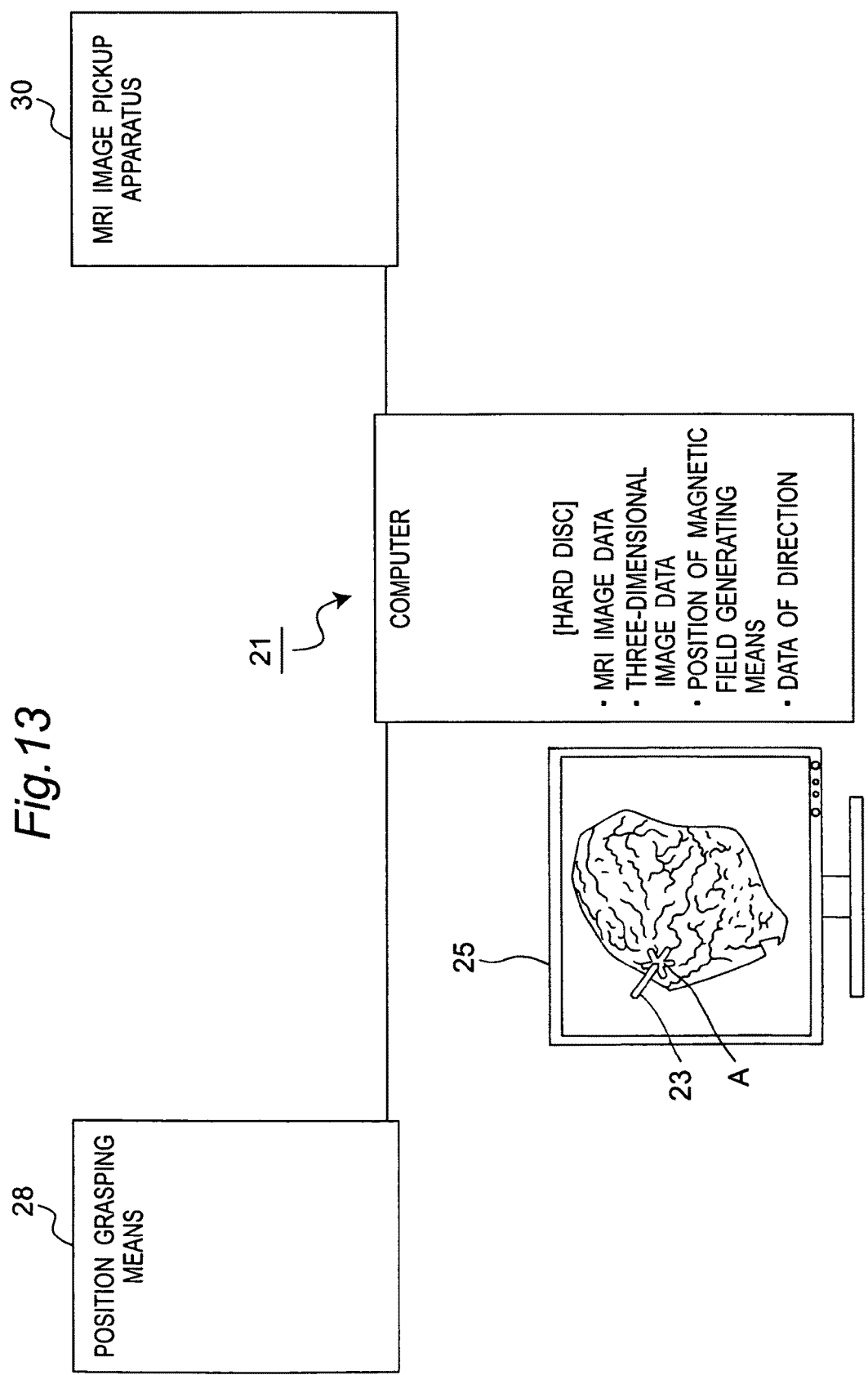
FIG. 13 is a block diagram showing a relation among a computer, an MRI image pickup apparatus, and position grasping means, which are used by the third embodiment according to the present invention.
Figure 14:
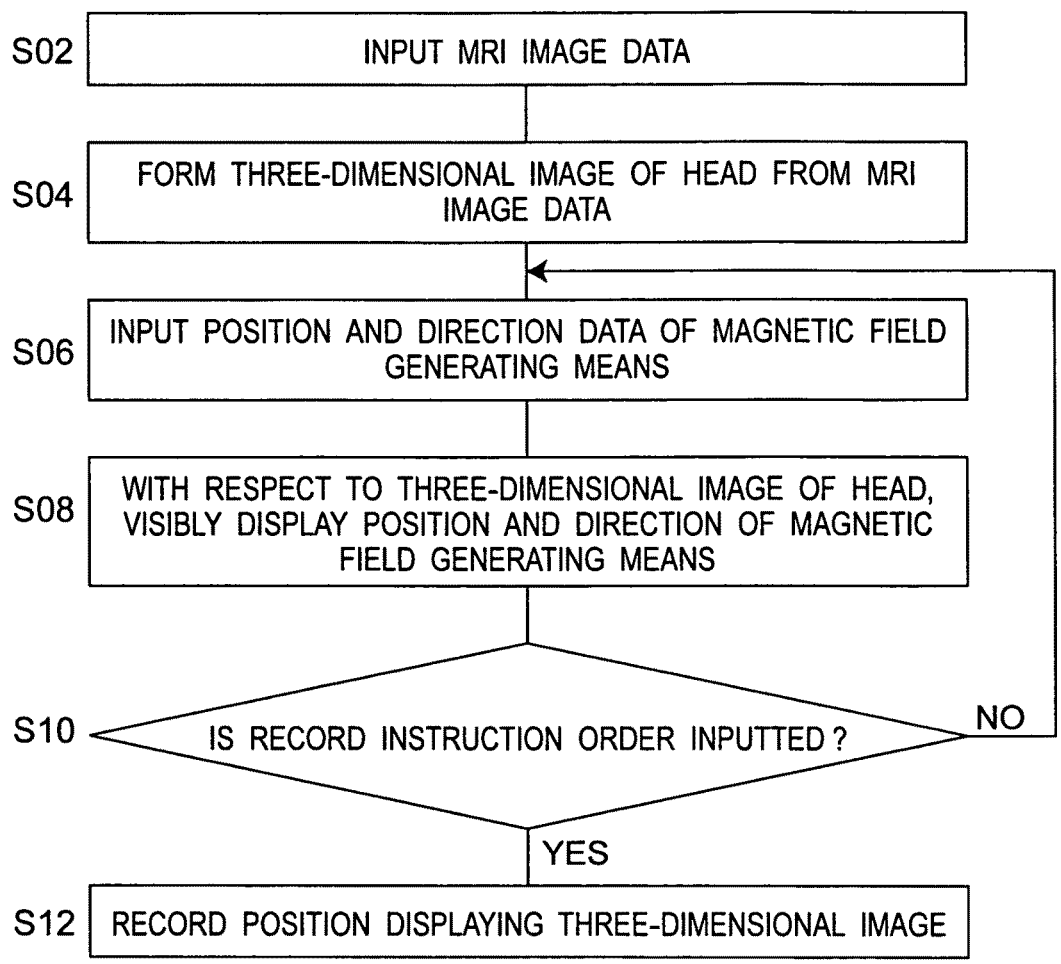
FIG. 14 is a schematic flow chart showing the operation of the computer to be used by the third embodiment according to the present invention.

Further, FIG. 13 is a block diagram showing a relation among the computer 21, a display 25, an MRI image pickup apparatus 30, and a position grasping means 28, which are used by the third embodiment according to the present invention. FIG. 14 is a schematic flow chart showing the operation of the computer 21 to be used by the third embodiment according to the present invention.

According to the method of manufacturing a fixture of the head according to a third embodiment of the present invention, at first, the detailed MRI image of the head of the examinee is taken by the MRI image pickup apparatus 30 to be sent to the computer 21 (FIG. 14, S02), and the computer 21 builds up a three-dimensional image relating to the head of the examinee based on this (FIG. 14, S04) (FIG. 12, Step 1). In the MRI image shooting in this time, the image is taken along many parallel planes to slice the head of the examinee thinly (at an interval of 1 to 2 mm). For example, the MRI image of the head may be taken along about 130 pieces of parallel planes at an interval of 2 mm, which are perpendicular to a center axis in a vertical direction of the head. Such an MRI image is hereinafter referred to as a "thin slice MRI image".

The computer 21 to be connected to the position grasping means 28 grasps in real time the data of the position and the direction of the magnetic field generating means 8 that are grasped by the position grasping means 28 (FIG. 14, S06). Further, the computer 21 calculates in real time the position, the direction and the angle of the brain (the cranium) of the examinee, and the positions, the directions, and the angles of the magnetic field generating means 8 and the generated magnetic field by using the above-described "thin slice MRI image" and displays them (FIG. 14, S08) (see FIGS. 3 and 13). In other words, adjusting a relation between a coordinate system of an MRI image and a coordinate system to be built up by the position grasping means 28 to grasp the position and the direction of the magnetic field generating means 8, the computer 21 superimposes the position and direction data of the movable magnetic field generating means on the MRI image and displays them (FIG. 12, Step 2).

The system that the computer 21 grasps the MRI image, the position of the head (the brain) of the examinee, a treatment bed, and the magnetic field generating means by connecting them; as described above, calculates in real time the position, the direction and the angle of the brain (the cranium), and the positions, the directions, and the angles of the magnetic field generating means 8 and the generated magnetic field; and displays them may be identical with those of the repetitive transcranial magnetic stimulator shown in FIG. 1 and the optical navigation guide system shown in FIG. 3, which are described in the first embodiment explained in the first embodiment.

Operating the transcranial magnetic stimulation control device 10 and the magnetic field generating means 8 while referring to the above-described displayed image and further, repeating an inquiry to the examinee and confirmation (FIG. 14, S06 to S08), the operator decides the relative positions, which are most effective for the examinee, of the magnetic field generating means 8 and of the generated magnetic field corresponding to the head of the examinee, and then, the operator instructs this decision to the computer 21 (FIG. 14, Step 10, Yes). For example, the displayed image of the display 25 shown in FIG. 13 shows the state in which the position represented by "A" is decided to be a position of the position of the most effective generated magnetic field. Upon receipt of the decision instruction, the computer 21 records the MRI three-dimensional image representing a positional relation between the brain, the cranium, and the magnetic field generating means 8 in this decision time as a position displaying three-dimensional image (FIG. 14, S12) (FIG. 12, Step 3).

Thus, by recording the position displaying three-dimensional image in the decision time, in the coordinate system of the three-dimensional image of the head of the examinee to be built up by the "thin slice MRI image", a specific numeral value relating to the position, the direction, and the angle of the magnetic field generating means 8 located at the optimum position, direction, and angle is given.

The above-described position displaying three-dimensional image is built up by the MRI image. Generally, the MRI image of the head includes not only the information of the shape and the position relating to the brain but also the information of the shape and the position relating to the cranium and the skin of the head. Therefore, if the information of the shape of the head of the examinee and the information relating to the position, direction, and angle of the magnetic field generating means are particularly taken from the information of the above-described position displaying three-dimensional image, the image information to depict the relative positional relation between the shape of the head of the examinee and the magnetic field generating means 8 three-dimensionally is formed (FIG. 12, Step 4).

The above-described image information to depict the relative positional relation three-dimensionally includes (1) the detailed shape information of the head of the examinee; (2) the detailed information of the shape of the nasal port and the shape of the ears; and (3) the information such that the strict relative position (the distance and the direction) of the magnetic field generating means to the target spot and the surface of the head of the examinee are quantified. Here, if an appropriate resin is used as a material, for example, due to the above-described information (1) and (2), an integrated-type of a fixture of the head (a helmet or the like) to be closed attached to and fit the head of the examinee can be generated. Further, due to the above-described information (3), it is possible to form a fixing part of a magnetic field generating means for always recreating the strict relative position of the magnetic field generating means with respect to the target spot of the examinee on the external face of this integral-type of the fixture of the head (FIG. 12, Step 5).

According to the above-described method for manufacturing the fixture of the head, as an image pickup apparatus for imaging the head of the examinee, the MRI image pickup apparatus is used, however, other image pickup apparatus may be used as far as the pickup image data can be used by the optical navigation guide system and the information of the shape and the position relating to the brain and the information of the shape and the position relating to the cranium and the skin of the head can be collected. For example, the image pickup apparatus may be a CT (Computed Tomography) apparatus and an ultrasonic apparatus or the like may be used.

In addition, the material of the fixture of the head to be manufactured by the method for manufacturing the fixture of the head according to the third embodiment of the present invention is not limited to a resin. Further, the fixture of the head to be generated is not limited to an integrated-type but may be configured by plural elements.

The invention claimed is:

1. A method for manufacturing a fixture of a head for fixing magnetic field generating means, comprising the steps of:
   taking an image of an object along parallel planes to form a plurality of image slices of the object;
   adjusting a relation between a coordinate system of the image and a coordinate system that is built up by a predetermined position grasping means that grasps a position and a direction of a movable magnetic field generating means and generates position and direction data;
   superimposing the position and direction data with respect to the image and forming a superimposed image;
   fixing the position and direction data at a specific point of time in the superimposed image;
   recording the fixed position and direction data and the superimposed image;
   obtaining first coordinate data that represent a surface data of the object based on the superimposed image recorded;
   obtaining second coordinate data that represent the position and direction of the magnetic field generating means based on the fixed position and direction data recorded;
   deciding relative relationship data that represent a relative relation between the surface of object and the magnetic field generating means based on the first coordinate data and the second coordinate data; and
   forming the fixture that comprises a magnetic field generating means fixing part at a relative position recorded of the magnetic field generating means based on the relative relationship data, such that the fixture is attachable to the surface of the object,
   wherein a relative positional relation of the magnetic field generating means, represented by the position and the direction data to be fixed in the recording step with respect to the object, is a positional relation such that the highest point of an intensity of an electric current to be induced by a magnetic field to be generated by the magnetic field generating means is constantly directed onto a target spot of a diameter not more than 10 mm, which is located at a primary motor cortex within a cranium, and
   wherein a direction of a magnetic field to be generated by the magnetic field generating means and a location of the target spot are made into a fixed relation.

2. The method for manufacturing a fixture of a head according to claim 1, wherein
   the image obtained by imaging the object is an MRI image.

3. A method for manufacturing a fixture of a head for fixing a magnetic field generating means, comprising:
   taking an image of an object along parallel planes to form a plurality of image slices of the object;
   adjusting a relation between a coordinate system of the image and a coordinate system that is built up by a predetermined position grasping means that grasps a position and a direction of a movable magnetic field generating means and generates positions and direction data;
   superimposing the position and direction data with respect to the image and forming a superimposed image;
   fixing the position and direction data at a specific point of time in the superimposed image;
   recording the fixed position and direction data and the superimposed image;
   obtaining first coordinate data that represent a surface data of the object based on the superimposed image recorded;
   obtaining second coordinate data that represent the position and direction of the magnetic field generating means based on the fixed position and direction data recorded;
   deciding relative relationship data that represent a relative position and angle between the surface of the object and the magnetic field generating means based on the first coordinate data and the second coordinate data; and
   forming the fixture that comprises a magnetic field generating means fixing part at a relative position recorded of the magnetic field generating means based on the relative relationship data such that the fixture is attachable to the surface of the object.

* * * * *